(12) United States Patent
Ron Edoute et al.

(10) Patent No.: US 8,868,204 B2
(45) Date of Patent: Oct. 21, 2014

(54) ESTHETIC DEVICE USEFUL FOR INCREASING SKIN BEAUTIFICATION AND METHODS THEREOF

(75) Inventors: Oded Ron Edoute, Tel Aviv (IL); Orit Ron Edoute, Tel Aviv (IL); Itzhak Kremin, Givatayim (IL); Vadim Polyakov, Petach Tikva (IL)

(73) Assignee: Venus Technologies Ltd., Tel Aviv (IL)

( * ) Notice: Subject to any disclaimer, the term of this patent is extended or adjusted under 35 U.S.C. 154(b) by 820 days.

(21) Appl. No.: 12/503,385

(22) Filed: Jul. 15, 2009

(65) Prior Publication Data

US 2010/0016850 A1    Jan. 21, 2010

Related U.S. Application Data

(60) Provisional application No. 61/080,699, filed on Jul. 15, 2008.

(51) Int. Cl.
*A61N 1/36* (2006.01)
*A61N 1/32* (2006.01)

(52) U.S. Cl.
CPC ..................... *A61N 1/328* (2013.01)
USPC ........................................................ 607/66

(58) Field of Classification Search
CPC ........... A61N 1/18; A61N 1/32; A61N 1/323; A61N 1/36; A61N 1/40; A61N 1/36014
USPC ........................ 607/2, 66–67, 148, 70, 72–73
See application file for complete search history.

(56) References Cited

U.S. PATENT DOCUMENTS

| | | | | |
|---|---|---|---|---|
| 3,851,651 A | * | 12/1974 | Icenbice, Jr. | 607/66 |
| 5,397,338 A | | 3/1995 | Grey et al. | |
| 5,527,357 A | * | 6/1996 | Springer, Jr. | 607/140 |
| 5,817,138 A | * | 10/1998 | Suzuki | 607/67 |
| 6,684,107 B1 | * | 1/2004 | Binder | 607/72 |
| 6,760,627 B2 | * | 7/2004 | Carter et al. | 607/69 |
| 7,110,826 B2 | | 9/2006 | Motoi | |
| 2002/0143365 A1 | * | 10/2002 | Herbst | 607/2 |
| 2008/0058915 A1 | * | 3/2008 | Chang | 607/140 |
| 2008/0195181 A1 | * | 8/2008 | Cole | 607/74 |
| 2009/0124958 A1 | * | 5/2009 | Li et al. | 604/20 |

* cited by examiner

*Primary Examiner* — Paula J Stice
(74) *Attorney, Agent, or Firm* — Martin Fleit; Paul D. Bianco; Fleit Gibbons Gutman Bongini & Bianco PL

(57) ABSTRACT

The present invention provides an esthetic device, useful for increasing skin beautification at a region of a patient's skin, comprising: a. electrical output device for repeatedly generating at least two electrical waveform simultaneously, each of said electrical waveform is comprised of a combination of multiple types of waveforms; and b. two electrodes electrically coupled to said electrical output device, placed on said skin region and apply said at least two electrical waveform on said skin portion. The two electrical signal applied to said region are essentially dissimilar, ultra-strong, at a frequency range of 0 Hz to 20 Hz, having an amplitude of about 4 to about 20 Volts, electrical current higher that 500 and lower than 2.5 milliampere and power output of about 24 milliWatts.

15 Claims, 13 Drawing Sheets

ESTHETIC DEVICE USEFUL FOR INCREASING SKIN BEAUTIFICATION AND METHODS THEREOF

FIELD OF THE INVENTION

This invention generally relates to a device used to improve skin viability and skin rejuvenation via electrotherapy, and a method of using the device.

BACKGROUND OF THE INVENTION

Improving the appearance of the skin has been the goal of many esthetic products and procedures for many years, since a tight skin, without wrinkles or cellulite, has a younger and more appealing appearance.

The skin and muscles of the face are structured differently than other places on the body. One side of the facial muscles is connected to the bone and the other to the skin. As the muscle deteriorates through the aging process, the attached facial skin loses it elasticity. Loss of elasticity causes the skin to sag and wrinkle. Strengthening relevant muscle groups restores and maintains the original shape and contour of the muscles. As facial muscles get stronger, they get shorter and flatter, causing the attached skin to become firmer, and smoothing wrinkles, improving facial appearance. Additionally, a contracting muscle's blood supply is 10 times greater than a muscle at rest. This fresh blood supply delivers vital oxygen and nutrients to the skin, revitalizing the tissue.

One way of exercising muscle groups which are not normally used, such as superficial facial muscles, is electrotherapy, which is the use of electrical currents applied to the skin by electrodes. The current flowing between the electrodes excites the muscles and the nerves leading to the muscles between those electrodes.

A specific type of electrotherapy, called micro-current electrical neuromuscular stimulation (MEMS), employs very small currents (in the range of microamperes), which result in almost no discomfort or sensation to the skin. They are becoming more widely accepted for the treatment of pain relief and tissue healing, by affecting the injured tissue at the cellular level [Gardner S E, Frantz R A, Schmidt F L (1999). "Effect of electrical stimulation on chronic wound healing: a meta-analysis". Wound Repair Regen 7 (6): 495-503].

Several devices have used electrotherapy for the purpose of skin rejuvenation and cosmetic treatment of wrinkles. Years of experience using those devices have shown that excitable tissues will accommodate to stimulation, unless the stimulation is dynamic to prevent accommodation.

Various methods of dynamic excitation have been proposed. The first relates to modulation of the input currents (varying sinusoidal waveform). Common modulation schemes include amplitude modulation (AM) in which the amplitude of the signal is varied, Frequency modulation (FM), in which the frequency of the signal is varied, and phase modulation (PM), in which the phase of the signal is varied.

Most electrotherapy devices base their input currents on pulses, usually square waveform pulses. These can also be modulated. Common modulation schemes for pulses include Pulse-code modulation (PCM), Pulse-width modulation (PWM), Pulse-amplitude modulation (PAM), Pulse-position modulation (PPM) and Pulse-density modulation (PDM). For example, patent application no. US 20005397338 discloses a device for delivering electrical energy to subcutaneous tissues for pain control and promotion of tissue healing using pulse width modulation scheme in which the pulse width is varied in a sinusoidal fashion from 60 microseconds to 170 microseconds.

Another method of modulating alternating pulses includes a predetermined combination of square pulses, not modulated by a mathematical formula. Such a combination is disclosed, for example, in U.S. Pat. No. 7,110,826. Furthermore U.S. Pat. No. 7,110,826 discloses electrical currents (of about 500 µA or less) that are similar to the humane body. Moreover, U.S. Pat. No. 7,110,826 discloses electrical voltage signals at the range of 0.3 V to about 3.9 V. The present invention, on the contrary, applies different electrical currents of about 1 milliampere, and voltages greater than 4V. Surprisingly, such signals were found to have a much greater esthetic effect on the skin. Furthermore, in the present application essentially different electrical currents are applied simultaneously on the skin for obtaining better esthetic results.

These various devices rely on the fact that even small differences in the current level, the method of excitation, the repetition of the excitation and the waveform may transform a therapeutic process to a harmful one. Therefore, the optimal use of electrotherapy depends more on experimentation than on theoretical design. The theory can only offer various solutions, but their efficacy can only be proven clinically.

Thus, there is still a long felt need for a device that uses a modulation scheme fit for improving skin viability and skin rejuvenation, relies on experimental or feedback loop for optimal results, easy to use, safe and complies with international safety standards.

SUMMARY OF THE INVENTION

It is one object of the present invention to provide an esthetic device, useful for increasing skin beautification at a region of a patient's skin, comprising:
  a. at least one electrical output device adapted to repeatedly generate at least two electrical signals simultaneously, each of said electrical signals is comprised of a combination of multiple types of waveforms; and,
  b. at least two electrodes coupled to said electrical output device, said at least two electrodes are placed on said skin region and are adapted to apply said at least two electrical signals on said skin portion;
  wherein said two electrical signal applied to said region are essentially dissimilar and selected from a group consisting of (i) electrical signal at a frequency range of about 0 Hz to about 20 Hz, especially 1.475 Hz, electrical current higher that about 500 µA and lower than about 2.5 milliampere, amplitude of about 4 to about 20 Volts and power output of about 24 milli-Watts; (ii) electrical signal at a frequency range of about 0 Hz to about 20 Hz, especially 0.5 Hz, electrical current higher that about 500 µA and lower than about 2.5 milliampere, amplitude of about 4 to about 20 Volts and power output of about 24 milli-Watts; (iii) electrical signal at a frequency range of about 0 Hz to about 20 Hz, especially 1 Hz, electrical current higher that about 500 µA and lower than about 2.5 milliampere, amplitude of about 4 to about 20 Volts and power output of about 24 milli-Watts or any combination thereof.

It is another object of the present invention to provide the skin beautification device as defined above, additionally comprising a controller coupled to said electrical signal generator, adapted to enable selection of each said electrical signals applied to said region.

It is another object of the present invention to provide the skin beautification device as defined above, wherein said selection is performed by patient.

It is another object of the present invention to provide the skin beautification device as defined above, wherein said controller additionally comprising a feedback mechanism, adapted to change said applied electrical signal according to predetermined medical needs.

It is another object of the present invention to provide the skin beautification device as defined above, wherein said electrical signal generator provides electrical signals in shapes selected in a non-limiting manner from a group consisting of triangular, rectangular, ramp, sinusoidal, composite, sawtooth shape or any combination thereof.

It is another object of the present invention to provide the skin beautification device as defined above, wherein said feedback mechanism additionally comprising:
  a. sensing means; adapted to sense electrotherapy parameters selected from a group consisting of dermal tensile forces, tissue impedance, muscle contraction forces, skin elasticity, a combination thereof, and any other parameter implying skin rejuvenation and viability; and,
  b. processing means, adopted to score analyzed tissue parameters according to a predetermined scale of treatment success; said parameters are selected from a group consisting of dermal tensile forces, tissue impedance, muscle contraction forces, skin elasticity, a combination thereof, and any other parameter implying skin rejuvenation and viability.

It is another object of the present invention to provide the skin beautification device as defined above, wherein said feedback mechanism additionally comprising:
  a. regulating means, adapted to allow said electrotherapy if said score is higher than a predetermined value and to stop said electrotherapy if said score is lower than a predetermined value.

It is another object of the present invention to provide the skin beautification device as defined above, wherein said electrical signal generator additionally comprising:
  a. processing means, adapted to store in a communicable database output waveform achieving highest scores; and
  b. processing means, adapted to regenerate upon command said output waveforms achieving highest scores.

It is another object of the present invention to provide the skin beautification device as defined above, wherein said feedback mechanism additionally comprising:
  a. processing means, adapted to store in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, tissue impedance, superficial muscle contractions or a combination thereof;
  b. sensing means; adapted to sense electrotherapy parameters selected from a group consisting of time t of time t of said treatment, temperature T of said tissue, duty cycle t/T, Frequency F, power P, tissue impedance, superficial muscle contractions or a combination thereof;
  c. regulating means, adapted to allow said electrotherapy if said parameters are within said safe treatment parameters and to stop said electrotherapy if said parameters are in said unsafe treatment parameters.

It is another object of the present invention to provide the skin beautification device as defined above, additionally comprising means for providing massage to said region of skin.

It is another object of the present invention to provide the skin beautification device as defined above, wherein said at least two electrodes are in a shape of a pair of gloves.

It is another object of the present invention to provide the skin beautification device as defined above, wherein said electrodes have needles capable of penetrating into subcutaneous tissue.

It is another object of the present invention to provide the skin beautification device as defined above, especially adapted to be applied in time ranges between 1 and about 99 minutes.

It is another object of the present invention to provide the skin beautification device as defined above, wherein the treatment repetition interval ranges between 1 to about 30 days.

It is another object of the present invention to provide the skin beautification device as defined above, wherein said device is especially adapted to operate according to IEC selected from a group consisting of IEC 60601-1-1, IEC 60601-1-2, IEC 60601-1-4, IEC 60601-1-6, IEC 60601-1-8, IEC 60601-2-3, IEC 60601-2-4, IEC 60601-2-9, IEC 60601-2-10, IEC 60601-2-25, IEC 60601-2-27, IEC 60601-2-35, IEC 60601-2-40, IEC 60601-2-47, IEC 60601-2-49, or any combination thereof.

It is another object of the present invention to provide the skin beautification device as defined above, wherein said region of a patient's skin is the face.

It is another object of the present invention to provide the skin beautification device as defined above, wherein the pain caused to the patient is less than 1 on the Wong-Baker faces pain rating scale.

It is another object of the present invention to provide a method of increasing skin beautification at a region of a patient's skin. The method comprises steps selected inters alia from of:
  a. obtaining a skin beautification device comprising:
    i. at least one electrical output device;
    ii. at least two electrodes coupled to said electrical output device;
  b. placing said electrodes on said skin region;
  c. providing simultaneously at least two dissimilar electrical signals;
  d. applying at least two electrical signals on said skin region; thereby increasing said beautification at a region of a patient's skin;
wherein said step of applying at least two electrical signals applies at least two essentially dissimilar electrical signals selected from a group consisting of (i) electrical signal at a frequency range of about 0 Hz to about 20 Hz, especially 1.475 Hz, electrical current higher that about 500 μA and lower than about 2.5 milliampere, amplitude of about 4 to about 20 Volts and power output of about 24 milli-Watts; (ii) electrical signal at a frequency range of about 0 Hz to about 20 Hz, especially 0.5 Hz, electrical current higher that about 500 μA and lower than about 2.5 milliampere, amplitude of about 4 to about 20 Volts and power output of about 24 milli-Watts; (iii) electrical signal at a frequency range of about 0 Hz to about 20 Hz, especially 1 Hz, electrical current higher that about 500 μA and lower than about 2.5 milliampere, amplitude of about 4 to about 20 Volts and power output of about 24 milli-Watts or any combination thereof.

It is another object of the present invention to provide the method as defined above, wherein the treatment time ranges between 1 and about 99 minutes.

It is another object of the present invention to provide the method as defined above, wherein the treatment repetition interval ranges between 1 to about 30 days.

It is another object of the present invention to provide the method as defined above, additionally comprising step of changing at least one of said applied electrical signal on said skin region according to predetermined medical needs.

It is another object of the present invention to provide the method as defined above, additionally comprising step of selecting said shape of said electrical signal from a group consisting of triangular, rectangular, ramp, sinusoidal, composite, sawtooth shape or any combination thereof.

It is another object of the present invention to provide the method as defined above, additionally comprising steps of:
(a) sensing electrotherapy parameters selected from a group consisting of dermal tensile forces, tissue impedance, muscle contraction forces, skin elasticity, a combination thereof, and any other parameter implying skin rejuvenation and viability; and,
(b) scoring analyzed tissue parameters according to a predetermined scale of treatment success; said parameters are selected from a group consisting of dermal tensile forces, tissue impedance, muscle contraction forces, skin elasticity, a combination thereof, and any other parameter implying skin rejuvenation and viability.

It is another object of the present invention to provide the method as defined above, additionally comprising step of allowing said electrotherapy if said score is higher than a predetermined value and to stop said electrotherapy if said score is lower than a predetermined value.

It is another object of the present invention to provide the method as defined above, additionally comprising steps of:
a. storing in a communicable database output waveform achieving highest scores; and,
b. regenerating upon command said output waveforms achieving highest scores.

It is another object of the present invention to provide the method as defined above, additionally comprising steps of:
a. storing in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, tissue impedance, superficial muscle contractions or a combination thereof;
b. sensing electrotherapy parameters selected from a group consisting of time t of time t of said treatment, temperature T of said tissue, duty cycle t/T, Frequency F, power P, tissue impedance, superficial muscle contractions or a combination thereof;
c. allowing said electrotherapy if said parameters are within said safe treatment parameters and to stop said electrotherapy if said parameters are in said unsafe treatment parameters.

It is another object of the present invention to provide the method as defined above, wherein said method is especially adapted to operate according to IEC selected from a group consisting of IEC 60601-1-1, IEC 60601-1-2, IEC 60601-1-4, IEC 60601-1-6, IEC 60601-1-8, IEC 60601-2-3, IEC 60601-2-4, IEC 60601-2-9, IEC 60601-2-10, IEC 60601-2-25, IEC 60601-2-27, IEC 60601-2-35, IEC 60601-2-40, IEC 60601-2-47, IEC 60601-2-49, or any combination thereof.

It is another object of the present invention to provide the method as defined above, additionally comprising step of applying massage to said region prior to and/or during and/or after said step of applying said electrical signal.

It is another object of the present invention to provide the method as defined above, additionally comprising step of applying said at least two electrical signals to the patient's face.

It is another object of the present invention to provide a synergic esthetic device, useful for increasing skin beautification at a region of a patient's skin. The device comprising inter alia:

a. at least one electrical output device adapted to repeatedly provide simultaneously at least two electrical signals selected from a group consisting of (i) first electrical signal at a frequency range of about 0 Hz to about 20 Hz, especially 1.475 Hz, electrical current higher that about 500 µA and lower than about 2.5 milliampere, and amplitude of about 4 to about 20 Volts and power output of about 24 milli-Watts; (ii) second electrical signal at a frequency range of about 0 Hz to about 20 Hz, especially 0.5 Hz, electrical current higher that about 500 µA and lower than about 2.5 milliampere, amplitude of about 4 to about 20 Volts and power output of about 24 milli-Watts; (iii) electrical signal at a frequency range of about 0 Hz to about 20 Hz, especially 1 Hz, electrical current higher that about 500 µA and lower than about 2.5 milliampere, amplitude of about 4 to about 20 Volts and power output of about 24 milli-Watts, or any combination thereof;
b. at least two electrodes coupled to said electrical output device adapted to be placed on said skin region and apply said at least two electrical signals on said skin portion;
wherein said device increases said skin beautification such that said increase is greater than the sum of said first signal increase and said second signal increase and said third signal increase.

It is another object of the present invention to provide the synergic esthetic device as defined above, additionally comprising a controller coupled to said electrical signal generator, adapted to enable selection of each said electrical signals applied to said region.

It is another object of the present invention to provide the synergic esthetic device as defined above, wherein said selection is performed by patient.

It is another object of the present invention to provide the synergic esthetic device as defined above, wherein said controller additionally comprising a feedback mechanism, adapted to change said applied electrical signal according to predetermined medical needs.

It is another object of the present invention to provide the synergic esthetic device as defined above, wherein said electrical signal generator provides electrical signals in shapes selected in a non-limiting manner from a group consisting of triangular, rectangular, ramp, sinusoidal, composite, sawtooth shape or any combination thereof.

It is another object of the present invention to provide the synergic esthetic device as defined above, wherein said feedback mechanism additionally comprising:
a. sensing means; adapted to sense electrotherapy parameters selected from a group consisting of dermal tensile forces, tissue impedance, muscle contraction forces, skin elasticity, a combination thereof, and any other parameter implying skin rejuvenation and viability; and,
b. processing means, adopted to score analyzed tissue parameters according to a predetermined scale of treatment success; said parameters are selected from a group consisting of dermal tensile forces, tissue impedance, muscle contraction forces, skin elasticity, a combination thereof, and any other parameter implying skin rejuvenation and viability.

It is another object of the present invention to provide the synergic esthetic device as defined above, wherein said feedback mechanism additionally comprising:
a. regulating means, adapted to allow said electrotherapy if said score is higher than a predetermined value and to stop said electrotherapy if said score is lower than a predetermined value.

It is another object of the present invention to provide the synergic esthetic device as defined above, wherein said electrical signal generator additionally comprising:
a. processing means, adapted to store in a communicable database output waveform achieving highest scores; and
b. processing means, adapted to regenerate upon command said output waveforms achieving highest scores.

It is another object of the present invention to provide the synergic esthetic device as defined above, wherein said feedback mechanism additionally comprising:
a. processing means, adapted to store in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, tissue impedance, superficial muscle contractions or a combination thereof;
b. sensing means; adapted to sense electrotherapy parameters selected from a group consisting of time t of time t of said treatment, temperature T of said tissue, duty cycle t/T, Frequency F, power P, tissue impedance, superficial muscle contractions or a combination thereof;
c. regulating means, adapted to allow said electrotherapy if said parameters are within said safe treatment parameters and to stop said electrotherapy if said parameters are in said unsafe treatment parameters.

It is another object of the present invention to provide the synergic esthetic device as defined above, additionally comprising means for providing massage to said region of skin prior to and/or during and/or after the treatment.

It is another object of the present invention to provide the synergic esthetic device as defined above, wherein said at least two electrodes are in a shape of a pair of gloves.

It is another object of the present invention to provide the synergic esthetic device as defined above, wherein said electrodes have needles capable of penetrating into subcutaneous tissue.

It is another object of the present invention to provide the synergic esthetic device as defined above, especially adapted to be applied in time ranges between 1 and about 99 minutes.

It is another object of the present invention to provide the synergic esthetic device as defined above, wherein the treatment repetition interval ranges between 1 to about 30 days.

It is another object of the present invention to provide the synergic esthetic device as defined above, wherein said device is especially adapted to operate according to IEC selected from a group consisting of IEC 60601-1-1, IEC 60601-1-2, IEC 60601-1-4, IEC 60601-1-6, IEC 60601-1-8, IEC 60601-2-3, IEC 60601-2-4, IEC 60601-2-9, IEC 60601-2-25, IEC 60601-2-27, IEC 60601-2-35, IEC 60601-2-40, IEC 60601-2-47, IEC 60601-2-49, or any combination thereof.

It is another object of the present invention to provide the synergic esthetic device as defined above, wherein said region of a patient's skin is the face.

It is another object of the present invention to provide the skin beautification device as defined above, wherein the pain caused to the patient is less than 1 on the Wong-Baker faces pain rating scale.

It is another object of the present invention to provide a method of synergic increasing skin beautification at a region of a patient's skin. The method comprising steps selected inter alia from:
a. obtaining a skin beautification device comprising:
   i. at least one electrical output device;
   ii. at least two electrodes coupled to said electrical output device;
b. placing said electrodes on said skin region;
c. providing simultaneously at least two essentially dissimilar electrical signals selected from a group consisting of (i) first electrical signal at a frequency of about 1.475 Hz, electrical current higher that about 500 µA and lower than about 2.5 milliampere, and amplitude of about 4-20 Volts and power output of about 24 milli-Watts; (ii) second electrical signal at a frequency of about 0.5 Hz, electrical current higher that about 500 µA and lower than about 2.5 milliampere, and amplitude of about 4-20 Volts and power output of about 24 milli-Watts; (iii) electrical signal at a frequency range of about 0 Hz to about 20 Hz, especially 1 Hz, electrical current higher that about 500 µA and lower than about 2.5 milliampere, amplitude of about 4 to about 20 Volts and power output of about 24 milli-Watts, or any combination thereof;
d. applying simultaneously said at least two electrical signals on said skin region; thereby increasing said beautification at a region of a patient's skin;
wherein said increasing of said skin beautification is greater than the sum of said first signal increase and said second signal increase and said third signal increase.

It is another object of the present invention to provide the method as defined above, wherein the treatment time ranges between 1 and about 99 minutes.

It is another object of the present invention to provide the method as defined above, wherein the treatment repetition interval ranges between 1 to about 30 days.

It is another object of the present invention to provide the method as defined above, additionally comprising step of changing said applied electrical signal on said skin according to predetermined medical needs.

It is another object of the present invention to provide the method as defined above, additionally comprising step of selecting said shape of said electrical signal from a group consisting of triangular, rectangular, ramp, sinusoidal, composite, sawtooth shape or any combination thereof.

It is another object of the present invention to provide the method as defined above, additionally comprising steps of:
(a) sensing electrotherapy parameters selected from a group consisting of dermal tensile forces, tissue impedance, muscle contraction forces, skin elasticity, a combination thereof, and any other parameter implying skin rejuvenation and viability; and,
(b) scoring analyzed tissue parameters according to a predetermined scale of treatment success; said parameters are selected from a group consisting of dermal tensile forces, tissue impedance, muscle contraction forces, skin elasticity, a combination thereof, and any other parameter implying skin rejuvenation and viability.

It is another object of the present invention to provide the method as defined above, additionally comprising step of allowing said electrotherapy if said score is higher than a predetermined value and to stop said electrotherapy if said score is lower than a predetermined value.

It is another object of the present invention to provide the method as defined above, additionally comprising steps of:
a. storing in a communicable database output waveform achieving highest scores; and,
b. regenerating upon command said output waveforms achieving highest scores.

It is another object of the present invention to provide the method as defined above, additionally comprising steps of:

a. storing in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, tissue impedance, superficial muscle contractions or a combination thereof;
b. sensing electrotherapy parameters selected from a group consisting of time t of time t of said treatment, temperature T of said tissue, duty cycle t/T, Frequency F, power P, tissue impedance, superficial muscle contractions or a combination thereof;
c. allowing said electrotherapy if said parameters are within said safe treatment parameters and to stop said electrotherapy if said parameters are in said unsafe treatment parameters.

It is another object of the present invention to provide the method as defined above, wherein said method is especially adapted to operate according to IEC selected from a group consisting of IEC 60601-1-1, IEC 60601-1-2, IEC 60601-1-4, IEC 60601-1-6, IEC 60601-1-8, IEC 60601-2-3, IEC 60601-2-4, IEC 60601-2-9, IEC 60601-2-10, IEC 60601-2-25, IEC 60601-2-27, IEC 60601-2-35, IEC 60601-2-40, IEC 60601-2-47, IEC 60601-2-49, or any combination thereof.

It is still an object of the present invention to provide the method as defined above, additionally comprising step of applying massage to said region prior to and/or during and/or after said step of applying said electrical signal It is lastly an object of the present invention to provide the method as defined above, additionally comprising step of applying said at least two electrical signals to the patient's face.

BRIEF DESCRIPTION OF FIGURES

In order to understand the invention and to see how it may be implemented in practice, a few preferred embodiments will now be described, by way of non-limiting example only, with reference to the accompanying drawings, in which.

DETAILED DESCRIPTION OF THE DRAWINGS

Figure 1A:
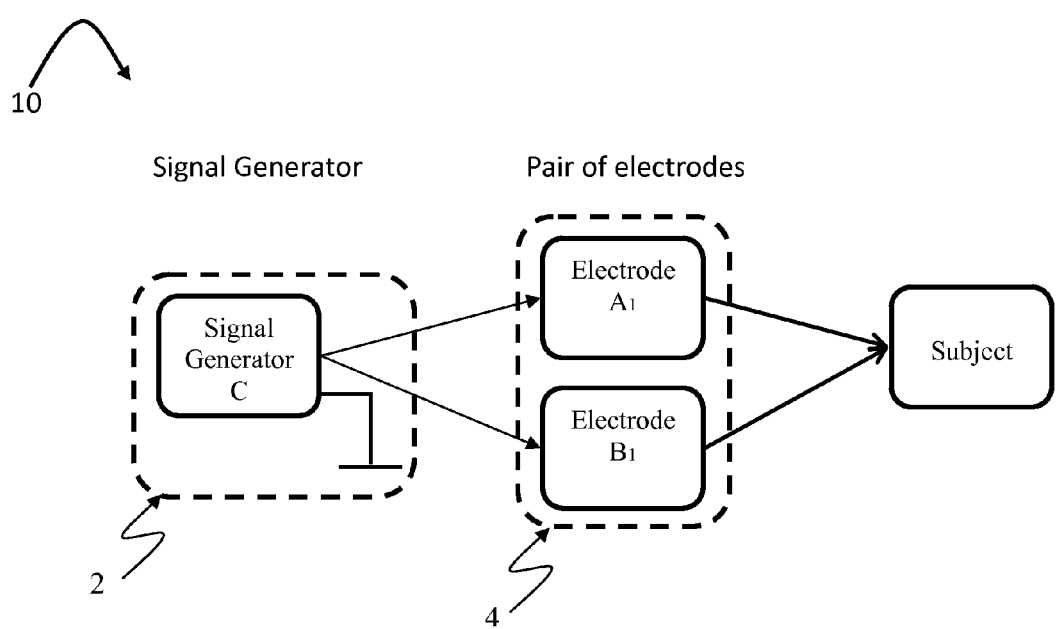
FIG. 1a-1c schematically presents the skin beautification device (10)

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and method for increasing skin beuatification.

The term "ultra-strong" refers hereinafter to electrical currents with high electrical voltage of about 4-20 volts, electrical signal at a frequency range of about 0 Hz to about 20 Hz, especially 1.475 Hz, electrical current higher that about 500 µA and lower than about 2.5 milliampere.

The term "electrotherapy" refers hereinafter in a non-limiting manner to the use of electrical currents applied to the skin by electrodes. In medicine, the term electrotherapy can apply to a variety of treatments, including the use of direct current in cardioversion and the use of electrical devices such as deep brain stimulators for neurological disease. The term has also been applied specifically to the use of electrical current to speed wound healing. Additionally, the term "electrotherapy" has also been applied to a range of alternative medical devices and treatments.

The term "basic waveform" refers hereinafter in a non-limiting manner to a single of a single shaped repeating waveform, such as sinusoidal, rectangular, ramp, triangular, composite or sawtooth shape.

The term "modulation" refers hereinafter in a non-limiting manner to variation of a property of an electromagnetic wave or signal, such as its amplitude, frequency, or phase.

The term "Amplitude modulation (AM)" refers hereinafter in a non-limiting manner to varying the amplitude of the modulated signal.

The term "Frequency modulation (FM)" refers hereinafter in a non-limiting manner to varying the frequency of the modulated signal.

The term "Phase modulation (PM)" refers hereinafter in a non-limiting manner to varying the phase of the modulated signal.

The term "Pulse modulation" refers hereinafter in a non-limiting manner to transferring a narrowband analog signal over an analog lowpass channel as a two-level quantized signal, by modulating a pulse train. Frequently used pulse modulation schems include Pulse-code modulation (PCM), Pulse-width modulation (PWM), Pulse-amplitude modulation (PAM), Pulse-position modulation (PPM) and Pulse-density modulation (PDM).

The term "beautification" refers herein after to skin tightening and lifting, smoothes wrinkles, stimulation of collagen re-growth, enrichment skin cells with oxygen and nutrition.

The term "International Electrotechnical Commission Standards (IEC) 60601-1" refers hereinafter to a medical electrical equipment standard. More specifically it refers to general requirements for basic safety and essential performance.

The term "IEC 60601-1-1" refers hereinafter to medical electrical equipment standard. More specifically it refers to general requirements for safety—Collateral standard: Safety requirements for medical electrical systems. The IEC 60601-1 set of standards are divided into three distinct areas. The first area is the basic standard IEC 60601-1. This is the general requirement for all electrical medical based products. The second area is the collateral standards, which cover across the board issues such as combining into a system with other devices, EMC, radiation protection, and programmable electronic medical systems (software, firmware, etc.). The standard numbers are IEC 60601-1-1, -1-2, -1-3, and -1-4 respectively. The third area is the particular standards that deal with a specific type of medical device. The particular standards are identified as IEC 60601-2-XX where XX identifies the particular standard number for the particular type of medical equipment. An example would be IEC 60601-2-3 which is the particular standard for short-wave therapy equipment.

The term "IEC 60601-1-2" refers hereinafter to medical electrical equipment standard. More specifically it refers to general requirements for basic safety and essential performance—Collateral standard: Electromagnetic compatibility—Requirements and tests.

The term "IEC 60601-1-4" refers hereinafter to medical electrical equipment standard. More specifically it refers to general requirements for safety—Collateral Standard: Programmable electrical medical systems.

The term "IEC 60601-1-6" refers hereinafter to medical electrical equipment standard. More specifically it refers to general requirements for basic safety and essential performance—Collateral standard: Usability.

The term "IEC 60601-1-8" refers hereinafter to medical electrical equipment standard. More specifically it refers to general requirements for basic safety and essential performance—Collateral Standard: General requirements, tests and guidance for alarm systems in medical electrical equipment and medical electrical systems.

The term "IEC 60601-2-3" refers hereinafter to medical electrical equipment standard. More specifically it refers to particular requirements for the safety of short-wave therapy equipment.

The term "IEC 60601-2-4" refers hereinafter to medical electrical equipment standard. More specifically it refers to particular requirements for the safety of cardiac defibrillators and cardiac defibrillators—monitors.

The term "IEC 60601-2-9" refers hereinafter to medical electrical equipment. More specifically it refers to particular requirements for the safety of patient contact dosemeters used in radiotherapy with electrically connected radiation detectors.

The term "IEC 60601-2-10" refers hereinafter to medical electrical equipment. More specifically it refers to particular requirements for the safety of nerve and muscle stimulators.

The term "IEC 60601-2-25" refers hereinafter to medical electrical equipment standard. More specifically it refers to particular requirements for the basic safety of electrocardiographs.

The term "IEC 60601-2-27" refers hereinafter to medical electrical equipment standard. More specifically it refers to particular requirements for the safety electrocardiographic monitoring equipment.

The term "IEC 60601-2-35" refers hereinafter to medical electrical equipment standard. More specifically it refers to particular requirements for the safety of blankets, pads and mattresses intended for heating in medical use.

The term "IEC 60601-2-40" refers hereinafter to medical electrical equipment standard. More specifically it refers to particular requirements for the safety of electromyographs and evoked response equipment.

The term "IEC 60601-2-47" refers hereinafter to medical electrical equipment standard. More specifically it refers to particular requirements for the safety, including essential performance, of ambulatory electrocardiographic systems.

The term "IEC 60601-2-49" refers hereinafter to medical electrical equipment standard. More specifically it refers to particular requirements for the safety of multifunction patient monitoring equipment.

The present invention provides devices and methods applying electrical signals to a desired region of the skin and enabling to achieve a skin tightening and lifting, and even smoothening wrinkles.

By simulating the natural electrochemical signals sent from the nervous system activates the facial muscles to contract and restructure. Since facial muscles are directly connected to the skin, contracting them will have an immediate effect on the facial laxity. The contraction of the facial muscles also increases blood circulation and stimulates collagen regeneration to nourish the skin.

The device as will be disclosed stimulates the muscles by applying cycles of individualized pulses through the nervous system directly into the muscle. By sending signals directly to the muscles, they contract faster and with more repetitions.

The stimulation of the muscles also increases blood circulation spreading more oxygen throughout the stimulation region.

As will be describe, one embodiment of the present invention allows the patient to control, combine, and make precise adjustment to all parameters, in order to suit the treatment to each and every patient in an effective, simple and fast way.

Reference is now made to FIG. 1a, illustrating the skin beautification device (10). The skin beautification device (10) is useful for increasing skin beautification at a region of a patient's skin. The device comprising in a non limiting manner the following:

(a) at least one electrical signal generator (2) adapted to provide simultaneously at least two substantially different electrical signals. In a preferred embodiment the electrical signal generator (2) comprises waveform generator (8) adapted to provide the different electrical signal's shapes.

(b) at least two electrodes (4) coupled to said electrical signal generator, adapted to be placed on said skin region and apply said at least two dissimilar electrical signal on said skin portion.

It is emphasized that the two electrical signal applied to said region are essentially dissimilar and selected from a group consisting of (i) electrical signal at a frequency range of about 0 Hz to about 20 Hz, especially 1.475 Hz, electrical current higher that about 500 μA and lower than about 2.5 milliampere, amplitude of about 4 to about 20 Volts and power output of about 24 milli-Watts; (ii) electrical signal at a frequency range of about 0 Hz to about 20 Hz, especially 0.5 Hz, electrical current higher that about 500 μA and lower than about 2.5 milliampere, amplitude of about 4 to about 20 Volts and power output of about 24 milli-Watts; (iii) electrical signal at a frequency range of about 0 Hz to about 20 Hz, especially 1 Hz, electrical current higher that about 500 μA and lower than about 2.5 milliampere, amplitude of about 4 to about 20 Volts and power output of about 24 milli-Watts or any combination thereof.

Surprisingly, it was found that applying simultaneously different electrical signals leads to better esthetic results. Furthermore, it was found the applying electrical voltage greater that about 4 V to about 20 V results in more effective cosmetic and/or esthetic results in the skin beautification. Yet more, it was found that applying electrical current higher than 500 μA and lower than about 2.5 milliampere; i.e., different from the biological electrical currents will also result in more effective cosmetic and/or esthetic results.

According to one embodiment of the present invention, the different electrical signals are applied to the face. The skin and muscles of the face are structured differently than other places on the body. One side of the facial muscles is connected to the bone and the other to the skin. As the muscle deteriorates through age the attached facial skin loses it elasticity. Loss of elasticity causes the skin to sag and wrinkle.

The device and method according to the present invention put the facial muscles through a series of stimulating workouts by painlessly causing the muscles to contract and build tissue fiber. The strengthened muscle fibers fill the skin out, making it tighter and more supple.

A contracting muscle's blood supply is 10 times greater than a muscle at rest. This fresh blood supply delivers vital oxygen and nutrients to the skin, revitalizing the tissue. The device and method of the present invention provides electro massaging to the skin which contracts the muscles as it stimulates collagen re-growth for firmer, smoother, and younger looking skin.

Figure 1B:
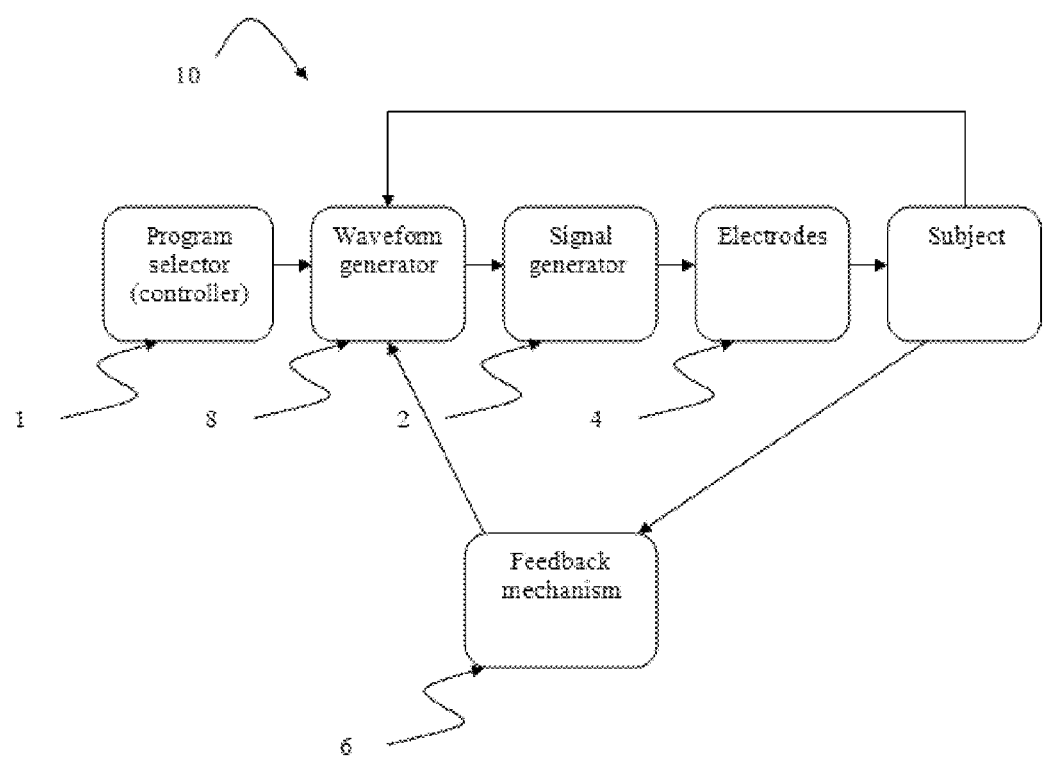

Reference is now made to FIG. 1b, illustrating the skin beautification device (10). As described above, the system comprising a program selector (1), a waveform generator (8), a signal generator (2), at least two electrodes (4), and a feedback mechanism (6).

The program selector (1) enables selecting one of several operation modes:
  a. A basic waveform, whose shape, amplitude, frequency and phase parameters are chosen randomly by the waveform generator (8);
  b. A combination of waveforms, whose shape, order of appearance, amplitude, frequency and phase parameters can be set by the user;
  c. A combination of waveforms, whose shape, order of appearance, amplitude, frequency and phase parameters are chosen randomly by the waveform generator (8);
  d. A basic waveform, whose shape, amplitude, frequency and phase parameters are fed by the feedback mechanism (6), according to scores attributed to previously used basic waveforms. The score results are collected from analyzing tissue parameters, consisting of, among others, dermal tensile forces, tissue impedance, muscle contraction forces, skin elasticity, a combination thereof, and any other parameter implying skin rejuvenation and viability.
  e. A basic waveform, whose shape, amplitude, frequency and phase parameters are fed by the feedback mechanism (6), according to scores attributed to previously used basic waveforms. The score results are fed to the feedback mechanism (6) as a number on a pre-set scale, according the subjects personal satisfaction with the treatments results.
  f. A combination of waveforms, whose order, shape, amplitude, frequency and phase parameters are fed by the feedback mechanism (6), according to scores attributed to previously used basic waveforms. The score results are collected from analyzing tissue parameters, consisting of, among others, dermal tensile forces, tissue impedance, muscle contraction forces, skin elasticity, a combination thereof, and any other parameter implying skin rejuvenation and viability.
  g. A combination of waveforms, whose order, shape, amplitude, frequency and phase parameters are fed by the feedback mechanism (6), according to scores attributed to previously used basic waveforms. The score results are fed to the feedback mechanism (6) as a number on a pre-set scale, according the subjects personal satisfaction with the treatments results.

The aim of the variety of operation modes is to deliver the best waveform or combination of waveforms to the subject, relying not only on mathematical theory, but mainly on empirical experience with the subjects individual skin, and its response to various signals, thus optimizing the beautification results. It should be emphasized that it is postulated that the shape of the waveform, not only its electrical parameters, influence the beautification results. Additionally, a synergistic effect of the combination of different basic waveforms is also postulated.

After the program has been set, the waveform generator (8) sets the desired signal through the signal generator (2), which transmits the signal to the applied electrodes (4). A feedback mechanism (6) assures the ability to improve the next treatment by updating and storing waveforms or waveform combinations achieving the highest scores on same or previous treatments.

Figure 1C:
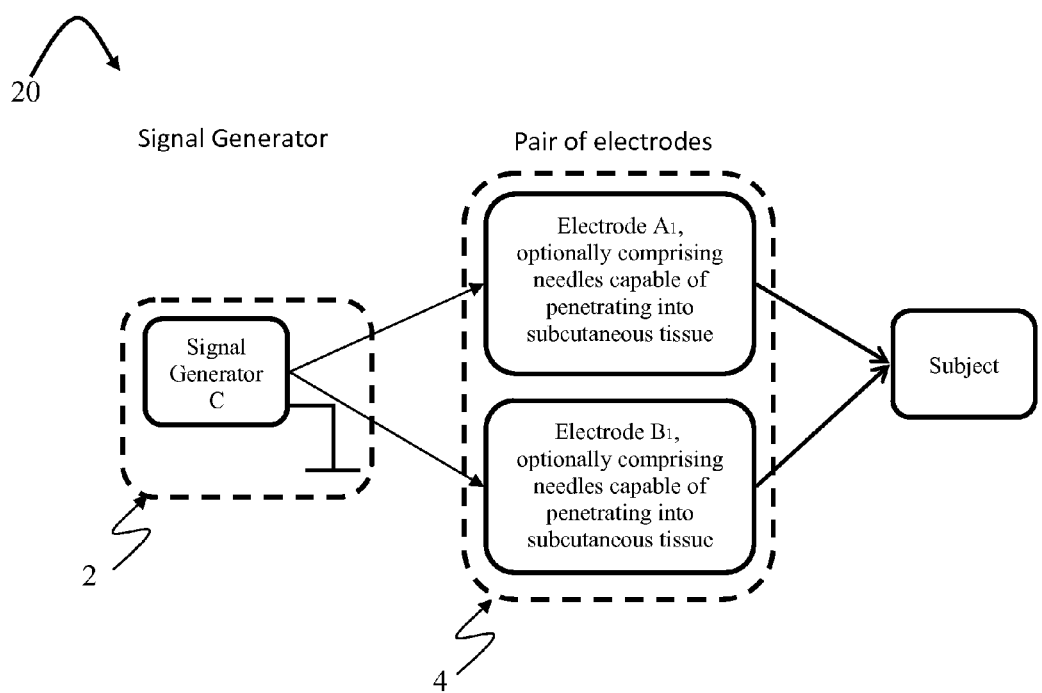

Reference is now made to FIG. 1*c*, illustrating another embodiment of the present invention. According to the embodiment, a synergic skin beautification device (20), useful for sinergically increasing skin beautification at a region of a patient's skin is provided.

The synergic skin beautification device (20) comprises, in a non limiting manner, the following:

(a) at least one electrical signal generator (i.e, electrical output device) 2. The electrical generator is adapted to repeatedly and simultaneously provide at least two electrical signals selected from a group consisting of (i) first electrical signal at a frequency of about 1.475 Hz, electrical current of about 1 milliampere, and amplitude of about 4-20 Volts and power output of about 24 milli-Watts; (ii) second electrical signal at a frequency of about 0.5 Hz, electrical current of about 1 milliampere, and amplitude of about 4-20 Volts and power output of about 24 milli-Watts; (iii) third electrical signal at a frequency of about 1 Hz, electrical, or any combination thereof;
  (b) at least two electrodes (4) coupled to said electrical signal generator adapted to be placed on said skin region and apply said at least two electrical signals on said skin portion.

By applying simultaneously at least two electrical signals, the device (20) increases said skin beautification such that said increase is greater than the sum of said first signal increase and said second signal increase and said third signal increase.

According to another embodiment of the present invention, each of the above mentioned devices (10 or 20) may additionally comprising a controller coupled to said electrical signal generator, adapted to enable selection of each said electrical signals applied to said region.

According to another embodiment of the present invention, the selection is performed by patient.

According to another embodiment of the present invention, the controller additionally comprises a feedback mechanism, adapted to change said applied electrical waveform according to predetermined medical needs.

According to another embodiment of the present invention, the electrical signal generator is further adapted to provide electrical signal in shapes selected in a non-limiting manner from a group consisting of triangular, rectangular, ramp, sinusoidal, composite, sawtooth shape or any combination thereof.

According to another embodiment of the present invention, the feedback mechanism additionally comprises:
  a. sensing means; adapted to sense electrotherapy parameters selected from a group consisting of dermal tensile forces, tissue impedance, muscle contraction forces, skin elasticity, a combination thereof, and any other parameter implying skin rejuvenation and viability; and,
  b. processing means, adopted to score analyzed tissue parameters according to a predetermined scale of treatment success; said parameters are selected from a group consisting of dermal tensile forces, tissue impedance, muscle contraction forces, skin elasticity, a combination thereof, and any other parameter implying skin rejuvenation and viability.

According to another embodiment of the present invention, the feedback mechanism additionally comprises regulating means, adapted to allow said electrotherapy if said score is higher than a predetermined value and to stop said electrotherapy if said score is lower than a predetermined value.

According to another embodiment of the present invention, the electrical signal generator additionally comprising:
  a. processing means, adapted to store in a communicable database output waveform achieving highest scores; and
  b. processing means, adapted to regenerate upon command said output waveforms achieving highest scores According to another embodiment of the present invention the electrical treatment is provided only in safe treatment parameters.

safe treatment parameters are defined by the parameters in table 1:

TABLE 1 safe treatment parameters

| parameter | Values |
| --- | --- |
| Time, t | 10 Minutes |
| Temperature, T | 25-80 Celsius |
| Frequency Hz | 0.5 |
| power P | 24 milli-Watt |

Unsafe safe treatment parameters are defined by the parameters in table 2:

TABLE 2 unsafe treatment parameters

| parameter | Values |
| --- | --- |
| Time, t | >10 hours (none stop) |
| Temperature, T | >80 Celsius |
| Frequency MHz | >10 Mhz |
| power P | >100 Watt |

According to another embodiment of the present invention, the feedback mechanism additionally comprises:
  a. processing means, adapted to store in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, tissue impedance, superficial muscle contractions or a combination thereof;
  b. sensing means; adapted to sense electrotherapy parameters selected from a group consisting of time t of time t of said treatment, temperature T of said tissue, Frequency F, power P, tissue impedance, superficial muscle contractions or a combination thereof;
  c. regulating means, adapted to allow said electrotherapy if said parameters are within said safe treatment parameters and to stop said electrotherapy if said parameters are in said unsafe treatment parameters.

According to another embodiment of the present invention, the feedback mechanism is the subject, and said feedback mechanism is the subject's satisfaction score from skin beautification results on a pre-set scale.

According to another embodiment of the present invention, the program of output waveform is chosen in a non limiting manner from a combination of waveforms, chosen by user, from a combination of waveforms achieving said highest scores, from a random series of waveforms, or from a combination thereof.

According to another embodiment of the present invention, the at least two electrodes are in a shape of a pair of gloves.

According to another embodiment of the present invention, the system further provides massage to said region of skin prior to and/or during and/or after the treatment.

According to another embodiment of the present invention, the electrodes have needles capable of penetrating into subcutaneous tissue.

According to another embodiment of the present invention, each of the above mentioned devices (10 or 20), are especially adapted to be applied in time ranges between 1 and about 99 minutes.

According to another embodiment of the present invention, the treatment repetition interval ranges between 1 and to 30 days.

According to another embodiment of the present invention, each of the above mentioned devices (10 or 20), are especially adapted to operate according to IEC selected from a group consisting of IEC 60601-1-1, IEC 60601-1-2, IEC 60601-1-4, IEC 60601-1-6, IEC 60601-1-8, IEC 60601-2-3, IEC 60601-2-4, IEC 60601-2-9, IEC 60601-2-10, IEC 60601-2-25, IEC 60601-2-27, IEC 60601-2-35, IEC 60601-2-40, IEC 60601-2-47, IEC 60601-2-49, of any combination thereof.

According to another embodiment of the present invention, each of the above mentioned devices (10 or 20), the pain caused to the patient is less than 1 on the Wong-Baker faces pain rating scale.

The devices as described above will have many advantages among other:
  (a) Immediate (within a few minutes) visible results;
  (b) Skin tightening and lifting;
  (c) Smoothes Wrinkles;
  (d) Stimulates collagen re-growth of cells;
  (e) will enrich skin cells with oxygen and nutrition; and,
  (f) Safe (according to different safety standards).

Figure 2A:
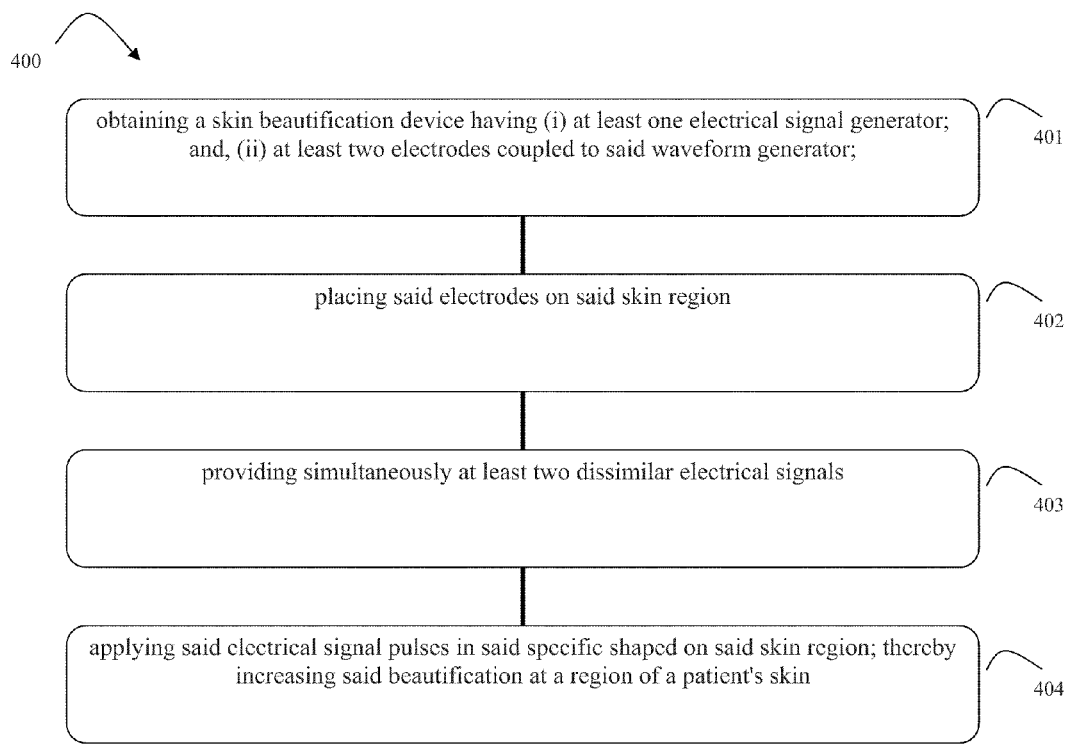
FIGS. 2a to 2d schematically illustrates methods for skin beuatification.

Reference is now made to FIG. 2a, schematically illustrating one possible method (400) of increasing skin beautification at a region of a patient's skin. The method comprising steps selected inter alia from:
  (a) obtaining a skin beautification device having (i) at least one electrical signal generator; and, (ii) at least two electrodes coupled to said waveform generator (step 401);
  (b) placing said electrodes on said skin region (step 402);
  (c) providing simultaneously at least two dissimilar electrical signals (step 403); and,
  (d) applying said electrical signal pulses in said specific shaped on said skin region; thereby increasing said beautification at a region of a patient's skin (step 404);

It is emphasized that the at least two dissimilar electrical signals provided by said step of providing are selected from (i) electrical signal at a frequency of about 1.475 Hz, electrical current of about 1 milliampere, and amplitude of about 4-20 Volts and power output of about 24 milli-Watts; (ii) electrical signal at a frequency of about 0.5 Hz, electrical current of about 1 milliampere, and amplitude of about 4-20 Volts and power output of about 24 milli-Watts; (iii) electrical signal at a frequency of about 1 Hz, electrical; or any combination thereof.

Figure 2B:
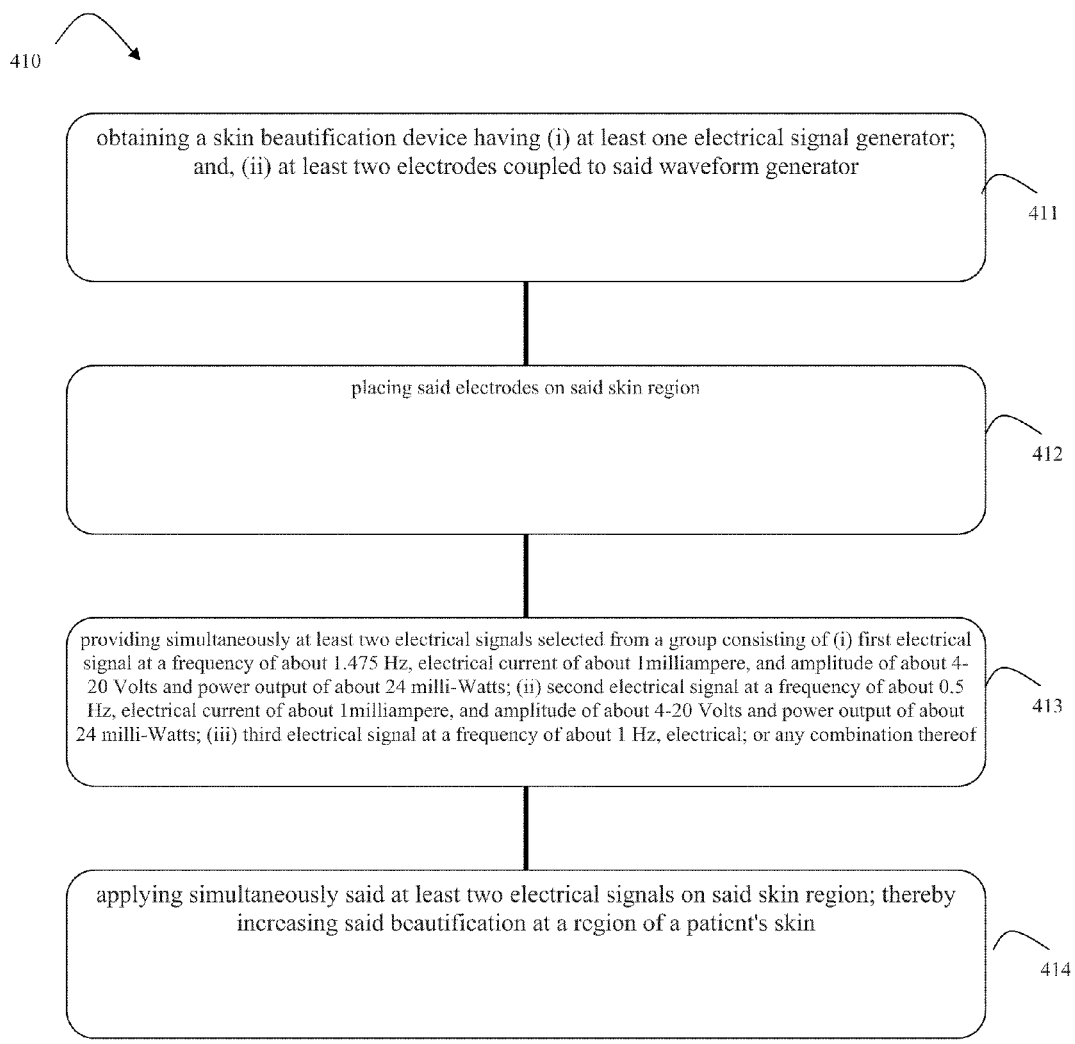

Reference is now made to FIG. 2b, schematically illustrating one possible method (410) of increasing skin beautification at a region of a patient's skin. The method comprising steps selected inter alia from:
  (a) obtaining a skin beautification device having (i) at least one electrical signal generator; and, (ii) at least two electrodes coupled to said waveform generator (step 411);
  (b) placing said electrodes on said skin region (step 412);
  (c) providing simultaneously at least two electrical signals selected from a group consisting of (i) first electrical signal at a frequency of about 1.475 Hz, electrical current of about 1 milliampere, and amplitude of about 4-20 Volts and power output of about 24 milli-Watts; (ii) second electrical signal at a frequency of about 0.5 Hz, electrical current of about 1 milliampere, and amplitude of about 4-20 Volts and power output of about 24 milli-Watts; (iii) third electrical signal at a frequency of about 1 Hz, electrical; or any combination thereof; and,
  (d) applying simultaneously said at least two electrical signals on said skin region; thereby increasing said beautification at a region of a patient's skin (step 414).

It is emphasized that said increasing of said skin beautification is greater than the sum of said first signal increase and said second signal increase and said third signal increase.

Figure 2C:
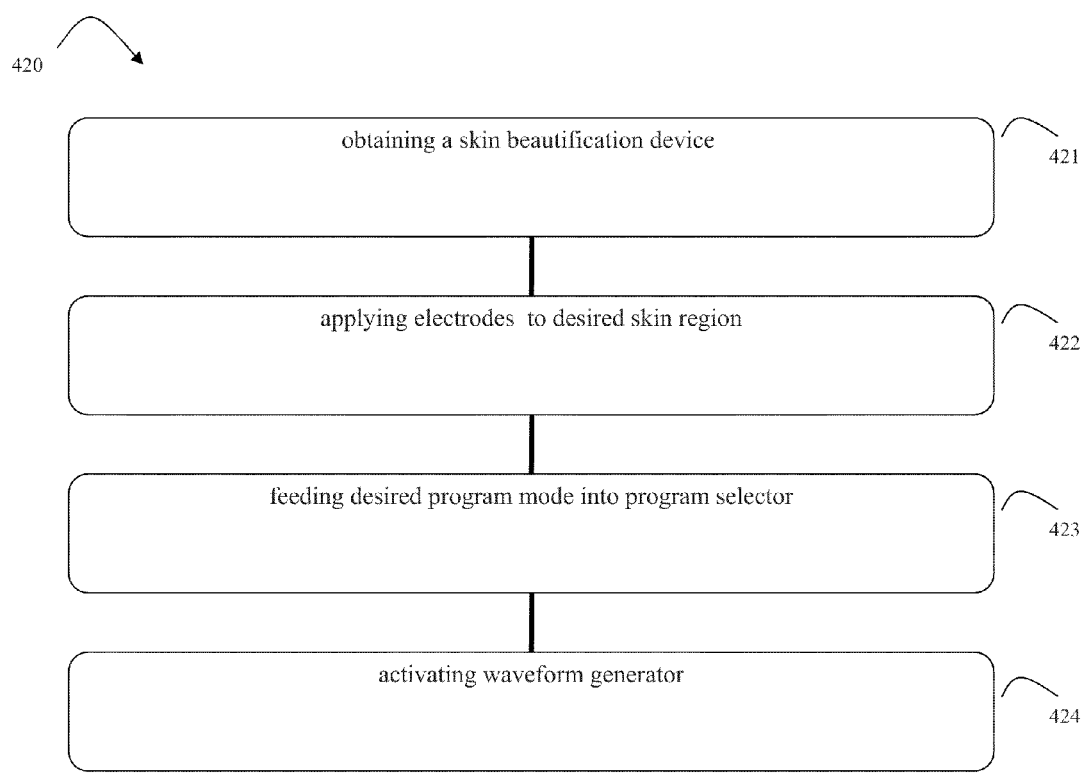

Reference is now made to FIG. 2c, schematically illustrating one possible method (420) of increasing skin beautification. The method comprising steps selected inter alia from obtaining a skin beautification device (either 10 or 20), applying electrodes (4) to desired skin region, feeding desired program mode into program selector (controller) (1)—i.e., selecting the desired shape of the electrical signal. The last step is activating the waveform generator (8).

Figure 2D:
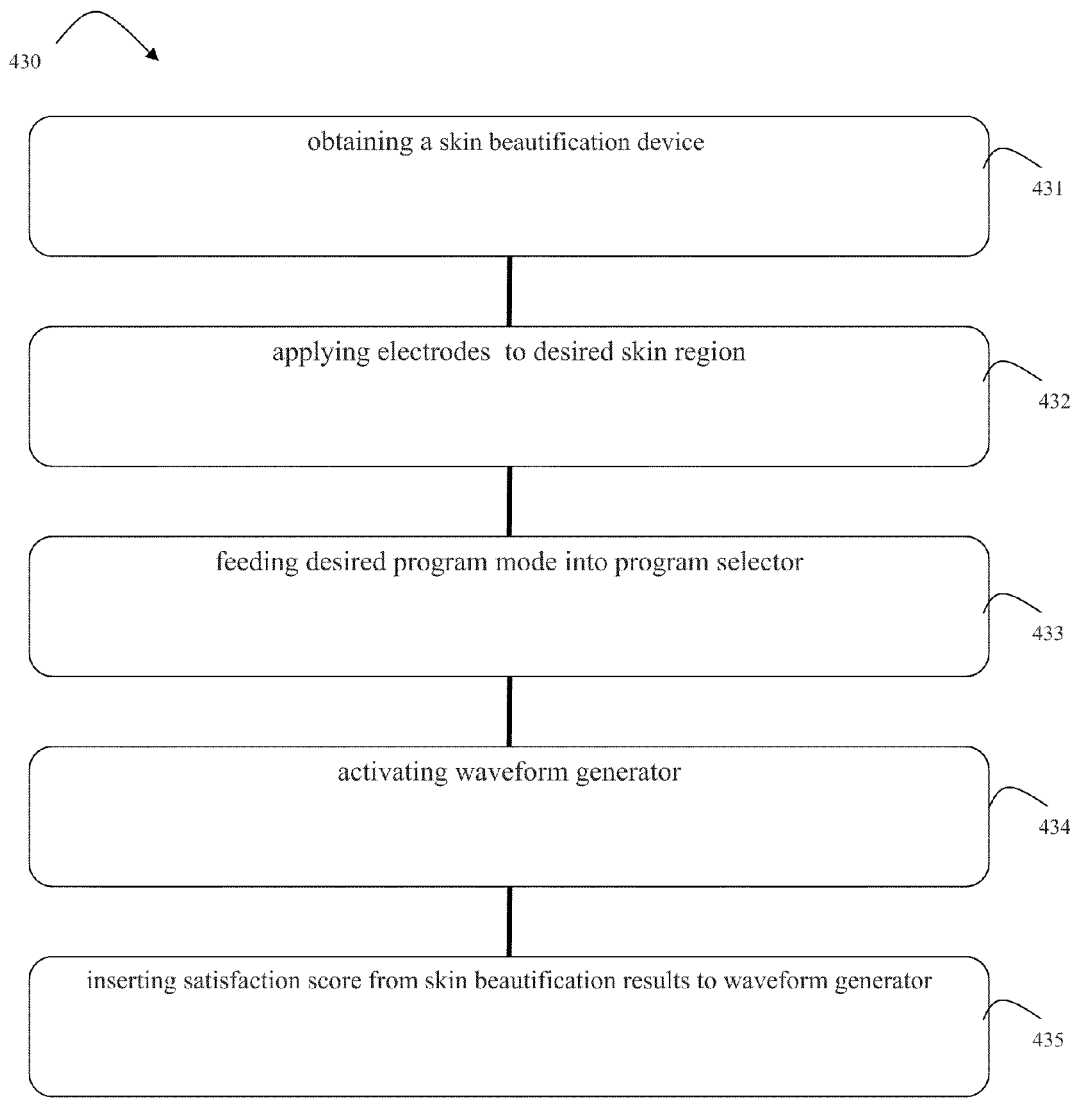

Reference is now made to FIG. 2d, schematically illustrating another possible method (430) of increasing skin beautification. The method comprising steps selected inter alia from obtaining a skin beautification device (either 10 or 20), applying electrodes (4) to desired skin region, feeding desired program mode into program selector (controller) (1) activating waveform generator (8) and inserting satisfaction score from skin beautification results to waveform generator (8).

According to one embodiment of the present invention, the treatment time of each of the methods (400-430) ranges between 1 and about 99 minutes.

According to one embodiment of the present invention, the treatment repetition interval of each of the methods (400-430) ranges between _1_ and about _30_ days.

According to one embodiment of the present invention, each of the above mentioned methods (400-430) additionally comprises step of changing said applied electrical signal on said skin according to predetermined medical needs.

According to one embodiment of the present invention, each of the above mentioned methods (400-430), additionally comprises step of selecting said shape of said electrical signal from a group consisting of triangular, rectangular, ramp, sinusoidal, composite, sawtooth shape or any combination thereof.

According to one embodiment of the present invention, each of the above mentioned methods (400-430) additionally comprising steps of:
(a) sensing electrotherapy parameters selected from a group consisting of dermal tensile forces, tissue impedance, muscle contraction forces, skin elasticity, a combination thereof, and any other parameter implying skin rejuvenation and viability; and,
(b) scoring analyzed tissue parameters according to a predetermined scale of treatment success; said parameters are selected from a group consisting of dermal tensile forces, tissue impedance, muscle contraction forces, skin elasticity, a combination thereof, and any other parameter implying skin rejuvenation and viability.

According to one embodiment of the present invention, each of the above mentioned methods (400-430) additionally comprises step of allowing said electrotherapy if said score is higher than a predetermined value and to stop said electrotherapy if said score is lower than a predetermined value.

According to one embodiment of the present invention, each of the above mentioned methods (400-430) additionally comprising steps of:
a. storing in a communicable database output waveform achieving highest scores; and,
b. regenerating upon command said output waveforms achieving highest scores.

According to one embodiment of the present invention, each of the above mentioned methods (400-430) additionally comprises steps of:
a. storing in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, tissue impedance, superficial muscle contractions or a combination thereof;
b. sensing electrotherapy parameters selected from a group consisting of time t of time t of said treatment, temperature T of said tissue, duty cycle t/T, Frequency F, power P, tissue impedance, superficial muscle contractions or a combination thereof;
c. allowing said electrotherapy if said parameters are within said safe treatment parameters and to stop said electrotherapy if said parameters are in said unsafe treatment parameters.

According to one embodiment of the present invention, each of the above mentioned methods (400-430) is especially adapted to operate according to IEC selected from a group consisting of IEC 60601-1-1, IEC 60601-1-2, IEC 60601-1-4, IEC 60601-1-6, IEC 60601-1-8, IEC 60601-2-3, IEC 60601-2-4, IEC 60601-2-9, IEC 60601-2-10, IEC 60601-2-25, IEC 60601-2-27, IEC 60601-2-35, IEC 60601-2-40, IEC 60601-2-47, IEC 60601-2-49, or any combination thereof.

According to one embodiment of the present invention, each of the above mentioned methods (400-430) may additionally comprise step of applying massage to said region prior to and/or during and/or after said step of applying said electrical signal.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

The following examples are illustration of a combination of two electrical signal applied on the skin for beautification.

Figure 3A:
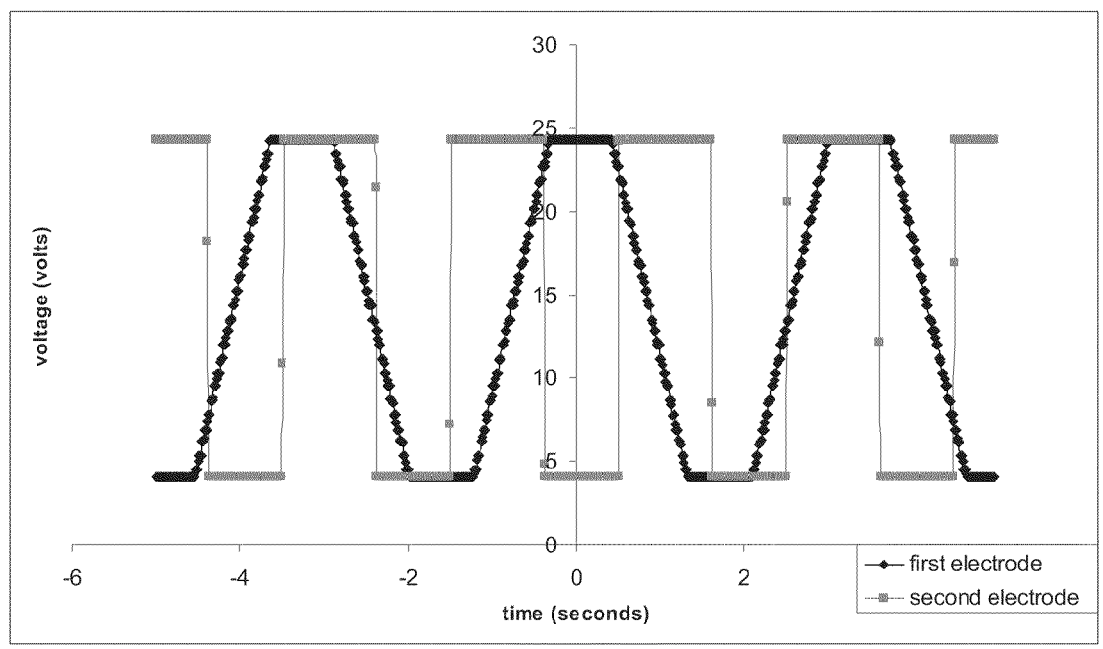
FIGS. 3a to 3f are examples of different electrical currents applied.

Reference is now made to FIG. 3a, which illustrates a first combination of two different electrical signals applied by the two electrodes. The figure illustrates how the voltage varies with time. The first signal is applied by the first electrode (denotes as first electrode) and the second electrical signal is applied by the second electrode (denotes as second electrode). As can be seen from the figure, the signal applied to the first electrode provides electrical signal at a frequency of 0.5 Hz, amplitude of about 4 to about 20 Volts and power output of about 24 mWatts. The second electrode provides electrical signal at a frequency of 1 Hz, amplitude of about 4 to about 20 Volts and power output of about 24 milli-Watts.

Figure 3B:
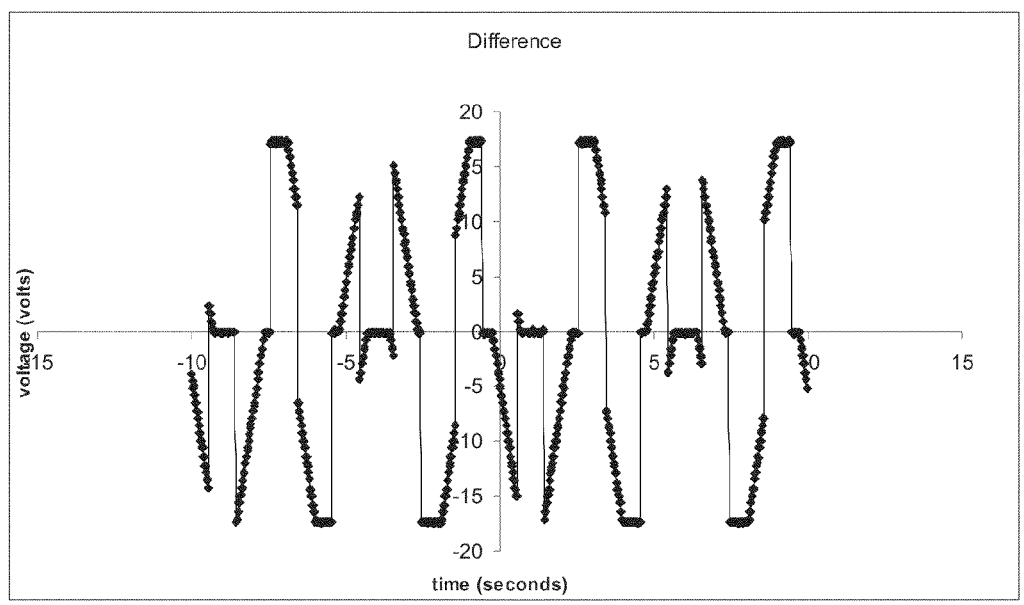

FIG. 3b illustrate the differences in the voltage applied between the two electrodes.

Figure 3C:
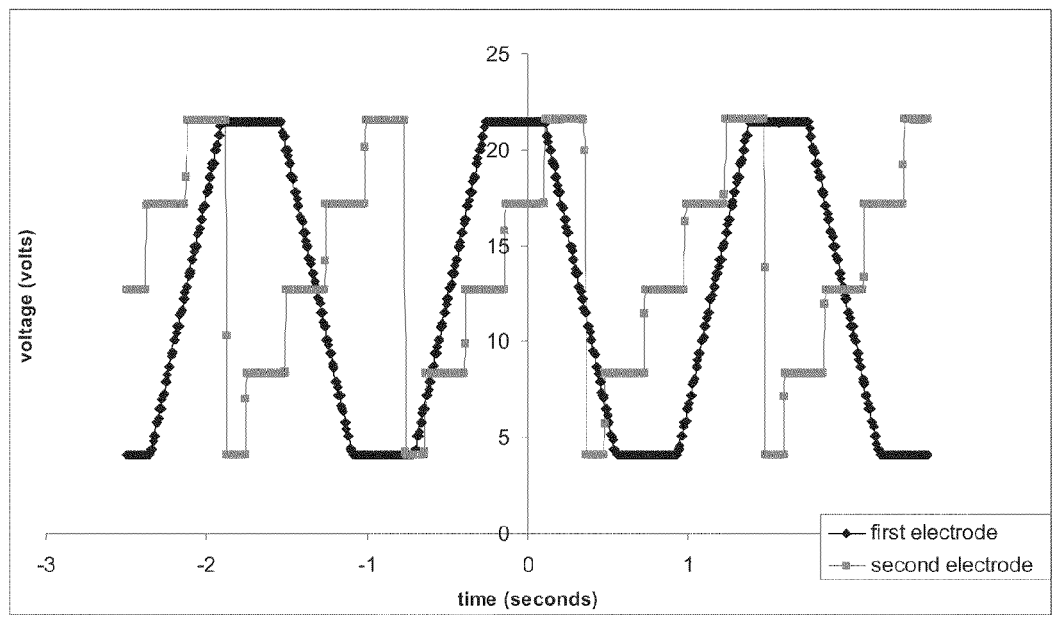

Reference is now made to FIG. 3c, which illustrates another combination of two different electrical signals applied by the two electrodes. The figure illustrates how the voltage varies with time. The first signal is applied by the first electrode (denotes as first electrode) and the second electrical signal is applied by the second electrode (denotes as second electrode). As can be seen from the figure, the signal applied to the first electrode provides electrical signal at a frequency of 0.5 Hz, amplitude of about 4 to about 20 Volts and power output of about 24 mWatts. The second electrode provides electrical signal at a frequency of 1 Hz, amplitude of about 4 to about 20 Volts and power output of about 24 milli-Watts.

Figure 3D:
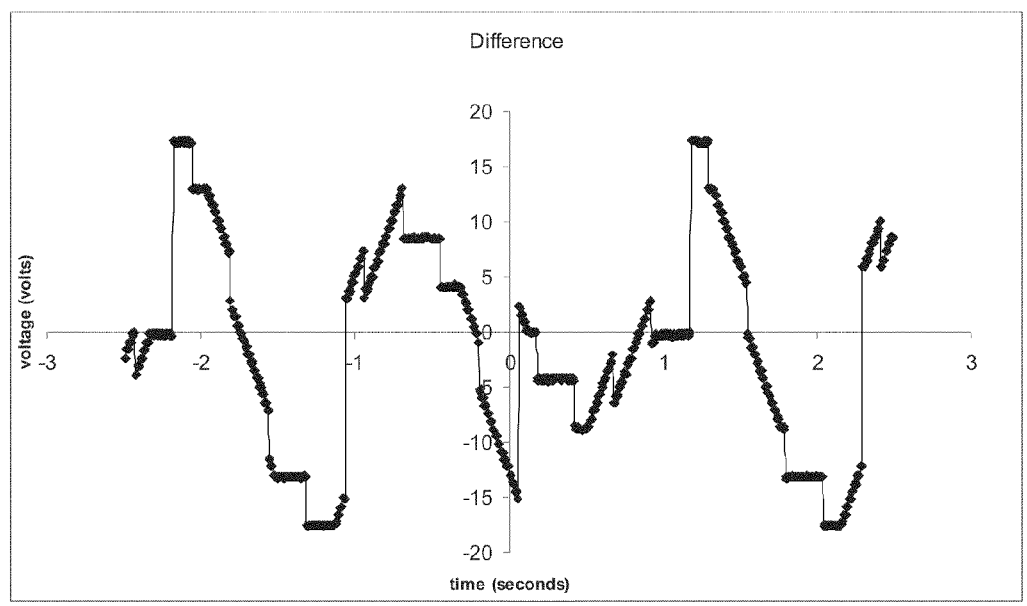

FIG. 3d illustrate the differences in the voltage applied between the two electrodes.

Figure 3E:
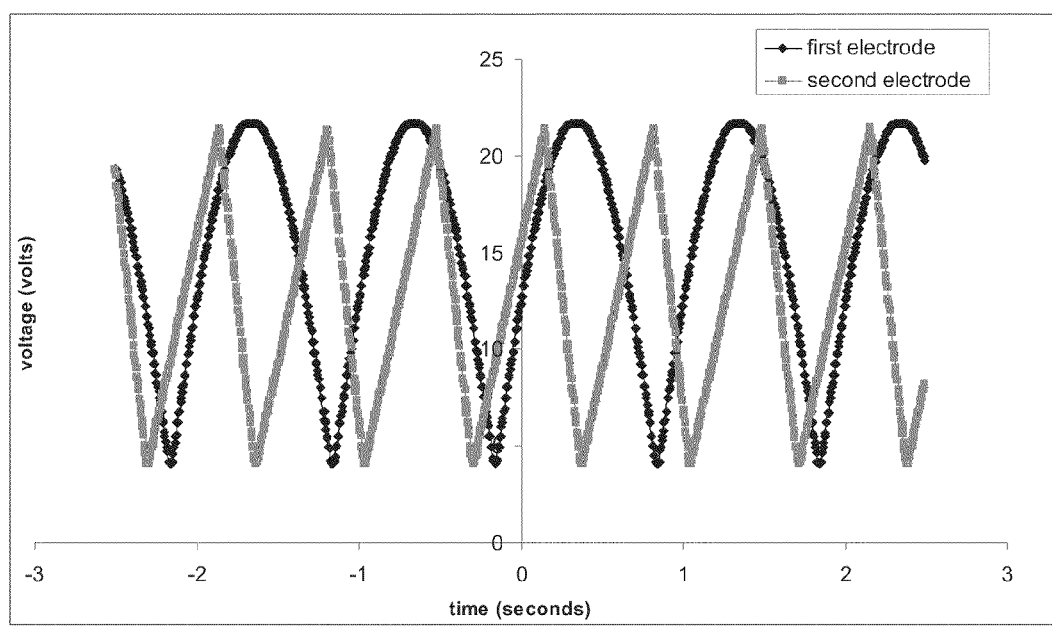

Reference is now made to FIG. 3e, which illustrates a first combination of two different electrical signals applied by the two electrodes. The figure illustrates how the voltage varies with time. The first signal is applied by the first electrode (denotes as first electrode) and the second electrical signal is applied by the second electrode (denotes as second electrode). As can be seen from the figure, the signal applied to the first electrode provides electrical signal at a frequency of 0.5 Hz, amplitude of about 4 to about 20 Volts and power output of about 24 mWatts. The second electrode provides electrical signal at a frequency of 1 Hz, amplitude of about 4 to about 20 Volts and power output of about 24 milli-Watts.

Figure 3F:
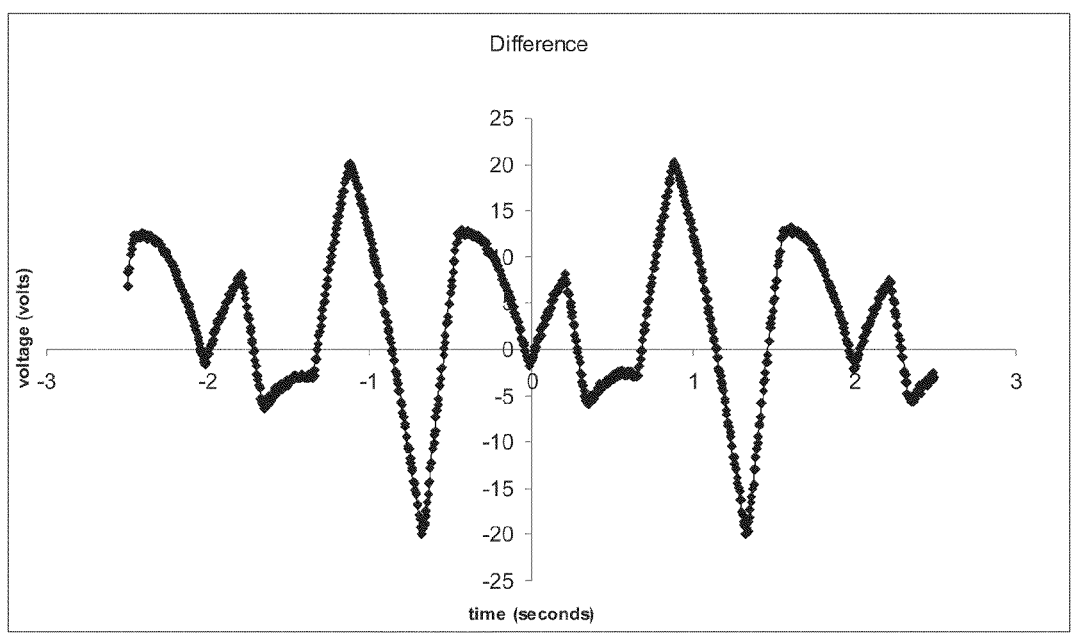

FIG. 3f illustrate the differences in the voltage applied between the two electrodes.

It should also be appreciated that the above described description of methods and apparatus are to be interpreted as including apparatus for carrying out the methods, and methods of using the apparatus of any type as well known to a person or ordinary skill, and which need not be described in detail herein for enabling a person of ordinary skill to practice the invention.

For the main embodiments of the invention, the particular selection of type and model is not critical, though where specifically identified, this may be relevant. The present invention has been described using detailed descriptions of embodiments thereof that are provided by way of example and are not intended to limit the scope of the invention. No limitation, in general, or by way of words such as "may", "should", "preferably", "must", or other term denoting a degree of importance or motivation, should be considered as a limitation on the scope of the claims or their equivalents unless expressly present in such claim as a literal limitation on its scope. It should be understood that features and steps described with respect to one embodiment may be used with other embodiments and that not all embodiments of the invention have all of the features and/or steps shown in a particular figure or described with respect to one of the embodiments. That is, the disclosure should be considered complete from combinatorial point of view, with each embodiment of each element considered disclosed in conjunction with each other embodiment of each element (and indeed in various combinations of compatible implementations of variations in the same element). Variations of embodiments described will occur to persons of the art. Furthermore, the terms "comprise," "include," "have" and their conjugates, shall mean, when used in the claims, "including but not necessarily limited to." Each element present in the claims in the singular shall mean one or more element as claimed, and when an option is provided for one or more of a group, it shall be interpreted to mean that the claim requires only one member selected from the various options, and shall not require one of each option. The abstract shall not be interpreted as limiting on the scope of the application or claims.

It is noted that some of the above described embodiments may describe the best mode contemplated by the inventors and therefore may include structure, acts or details of structures and acts that may not be essential to the invention and which are described as examples. Structure and acts described herein are replaceable by equivalents performing the same function, even if the structure or acts are different, as known in the art. Therefore, the scope of the invention is limited only by the elements and limitations as used in the claims.

The invention claimed is:

1. A non-gliding-esthetic device for increasing skin beautification at a region of a patient's skin, comprising:
   at least one electrical output device to which at least two electrodes are electrically coupled, said at least one electrical output devices configured to generate treatment of at least one portion of said skin; said treatment comprising a combination of at least two simultaneously generated electrical signals, each of said at least two electrical signals comprising a continuously repeating basic electrical waveform, each of said continuously repeating basic electric waveforms individually applied by the at least two electrodes
   wherein:
      each of said continuously repeating basic electrical waveforms is ultra-strong and characterized by a frequency of 20 Hz or less and at least one characteristic chosen from the group consisting of a current of between 500 µA and 2.5 mA and an amplitude of between about 4 V and about 20 V;
      each of said continuously repeating basic electrical waveforms differs from the others in at least one characteristic chosen from the group consisting of frequency, amplitude, current, and shape, at least one of said electrical waveforms differing from a square wave; and,
      further wherein said non-gliding esthetic device is configured to remain stationary on said patients skin during said treatment.

2. The skin beautification device according to claim 1, additionally comprising a controller coupled to said at least one electrical output device, adapted to enable selection of at least one of frequency, amplitude, current, and shape of each said electrical signal applied to said region; said selection is performed by said patient or by a physician.

3. The skin beautification device according to claim 2, wherein said controller is further adapted to change at least one of said at least two applied electrical signals according to predetermined medical needs, said controller additionally comprising:
   a feedback mechanism adapted to sense electrotherapy parameters selected from the group consisting of dermal tensile forces, tissue impedance, muscle contraction forces, skin elasticity, and any other parameter correlating with skin rejuvenation and viability; and
   a processor adapted to (a) score analyzed tissue parameters according to a predetermined scale of treatment success; said parameters selected from the group consisting of dermal tensile forces, tissue impedance, muscle contraction forces, skin elasticity, and any other parameter correlating with skin rejuvenation and viability; and, (b) allow said electrotherapy if said score is higher than a predetermined value and to stop said electrotherapy if said score is lower than a predetermined value.

4. The skin beautification device according to claim 1, wherein each of said continuously repeating electrical waveforms is selected from the group consisting of triangular, rectangular, ramp, sinusoidal, and any combination thereof.

5. The skin beautification device according to claim 4, wherein said controller further comprises:
   a processor adapted to (a) store in a communicable database predetermined parameters defining (i) safe treatment parameters and (ii) unsafe treatment parameters; said parameters selected from the group consisting of time t of said treatment, temperature T of said tissue, duty cycle, frequency F, power P, tissue impedance, superficial muscle contractions and a combination thereof and (b) allow said electrotherapy if said parameters are within said safe treatment parameters and to stop said electrotherapy if said parameters are in said unsafe treatment parameters; and
   a feedback mechanism adapted to sense electrotherapy parameters selected from the group consisting of time t of said treatment, temperature T of said tissue, duty cycle, frequency F, power P, tissue impedance, superficial muscle contractions and a combination thereof.

6. The skin beautification device according to claim 1, additionally comprising means for providing massage to said region of skin.

7. The skin beautification device according to claim 1, wherein said electrodes comprise at least one needle for penetrating into subcutaneous tissue.

8. The skin beautification device according to claim 1, wherein each of said electrical waveforms is characterized by a frequency chosen from the group consisting of about 1.475 Hz; about 1 Hz; and about 0.5 Hz.

9. A method of increasing skin beautification at a region of a patient's skin, said method comprising:
placing at least two electrodes on said skin region; and
applying treatment to at least one region of the skin; said treatment comprising simultaneously applying at least two electrical signals to said skin region via said at least two electrodes, each of said at least two electrical signals comprising an ultra-strong continuously repeating basic electrical waveform having a frequency of 20 Hz or less and at least one characteristic chosen from the group consisting of a current of between 500 μA and 2.5 mA and an amplitude of between about 4 V and about 20 V, each of said continuously repeating basic electrical waveforms individually applied by the at least two electrodes
wherein
each of said continuously repeating basic electrical waveforms within said treatment differs from the others in at least one characteristic chosen from the group consisting of frequency, amplitude, current, and shape, at least one of said electrical waveforms differing from a square wave; and
further wherein said electrodes remain stationary on said patient's skin during said treatment.

10. The method according to claim 9, additionally comprising a step of changing at least one of said applied electrical signals on said skin region according to predetermined medical needs.

11. The method according to claim 9, additionally comprising:
sensing electrotherapy parameters selected from the group consisting of dermal tensile forces, tissue impedance, muscle contraction forces, skin elasticity, and any other parameter correlating with skin rejuvenation and viability;
scoring analyzed tissue parameters according to a predetermined scale of treatment success, said parameters selected from the group consisting of dermal tensile forces, tissue impedance, muscle contraction forces, skin elasticity, and any other parameter correlating with skin rejuvenation and viability; and,
allowing said electrotherapy if said score is higher than a predetermined value and to stop said electrotherapy if said score is lower than a predetermined value.

12. The method according to claim 9, additionally comprising a step of applying massage to said region at a time chosen from the group consisting of prior to said step of applying said electrical signal; during said step of applying said electrical signal; and after said step of applying said electrical signal.

13. The method according to claim 9, additionally comprising steps of:
storing in a communicable database predetermined parameters defining (i) safe treatment parameters and (ii) unsafe treatment parameters, said parameters selected from a group consisting of time t of said treatment, temperature T of said tissue, duty cycle, frequency F, power P, tissue impedance, superficial muscle contractions, and a combination thereof;
sensing electrotherapy parameters selected from a group consisting of time t of said treatment, temperature T of said tissue, duty cycle, frequency F, power P, tissue impedance, superficial muscle contractions and a combination thereof; and
allowing said electrotherapy if said parameters are within said safe treatment parameters and to stop said electrotherapy if said parameters are in said unsafe treatment parameters.

14. The method according to claim 9, wherein each of said electrical waveforms is characterized by a frequency chosen from the group consisting of about 1.475 Hz; about 1 Hz; and about 0.5 Hz.

15. The method according to claim 9, additionally comprising obtaining a skin beautification device comprising at least one electrical signal generator for simultaneous generation of at least two electrical signals, each of said electrical signals comprising a different continuously repeating basic electrical waveform and at least two electrodes, each of which is electrically coupled to one of said at least one electrical signal generators.

* * * * *